United States Patent [19]

Mikhail

[11] Patent Number: 5,222,955
[45] Date of Patent: Jun. 29, 1993

[54] METHOD FOR IMPLANTING A PATELLAR PROSTHESIS

[76] Inventor: W. E. Michael Mikhail, 4203 Shamley Green, Toledo, Ohio 43623

[21] Appl. No.: 830,309

[22] Filed: Jan. 31, 1992

Related U.S. Application Data

[63] Continuation-in-part of Ser. No. 652,882, Feb. 8, 1991, Pat. No. 5,180,384.

[51] Int. Cl.⁵ ............................................. A61B 19/00
[52] U.S. Cl. ........................................ 606/80; 623/20
[58] Field of Search ................. 623/16, 18, 20, 22, 623/23; 606/80, 88, 96

[56] References Cited

U.S. PATENT DOCUMENTS

| | | |
|---|---|---|
| 3,878,566 | 4/1975 | Bechtol . |
| 4,158,894 | 6/1979 | Worrell . |
| 4,341,206 | 7/1982 | Perrett et al. ............... 606/96 |
| 4,686,972 | 8/1987 | Kurland . |
| 4,860,735 | 8/1989 | Davey et al. . |
| 4,919,673 | 4/1990 | Willert et al. . |
| 4,919,679 | 4/1990 | Averill et al. . |
| 4,982,730 | 1/1991 | Lewis, Jr. ..................... 604/22 |
| 5,061,287 | 10/1991 | Feiler . |

OTHER PUBLICATIONS

"Surgical Procedure for The Whiteside Ortholoc Modular Knee System", Brochure published by Dow Corning Wright.
Article Entitled "Economy is the mother of a cement removal technique", *Orthopedics Today*, pp. 18 & 19, Sep. 1989.
Brochure published by Johnson & Johnson Orthopaedics entitled "Patellar Resurfacing with Specialist ® Instruments in Total Knee Arthroplasty-Surgical Technique".
Brochure published by Dow Corning Wright entitled "Whiteside Ortholoc ® Modular Knee System".
Brochure published by Intermedics Orthopedics entitled "Surgical Technique The Intermedics Natural-Knee System".
Brochure published by DePuy, Division of Boehringer Mannheim Corporation, Warsaw, Ind., p. 25.

*Primary Examiner*—David J. Isabella
*Assistant Examiner*—Gina M. Gualtieri
*Attorney, Agent, or Firm*—Emch, Schaffer, Schaub & Porcello Co.

[57] ABSTRACT

A method for preparing a patella for receiving a patellar implant and for implanting a prosthesis therein. An elongated passageway is drilled completely through formed in the patella which is then reamed to form a cavity of a size and configuration to receive the patellar prosthesis using a cannulated reamer telescoped over a guide rod positioned in the elongated passageway. Centering means may be provided for supporting the guide rod. During implantation of the prosthesis, excess marrow fat, blood and debris may escape through the passageway outlet. The second opening acts as a vent to allow optimal cement pressurization and fixation (osseointegrating) and sound patellar prosthesis fixation to the reamed cavity.

21 Claims, 8 Drawing Sheets

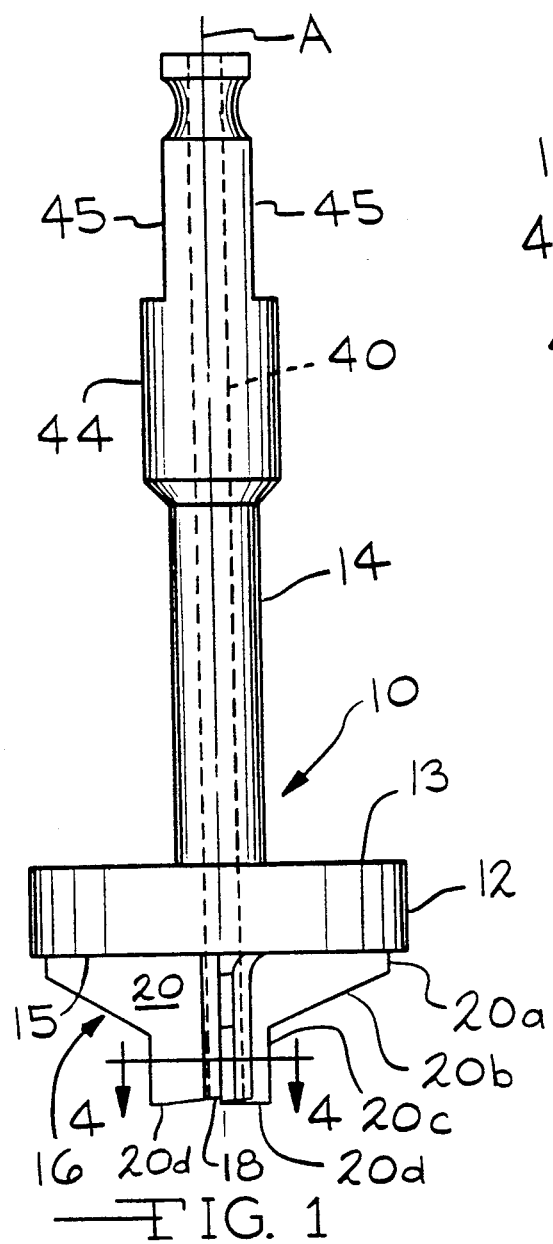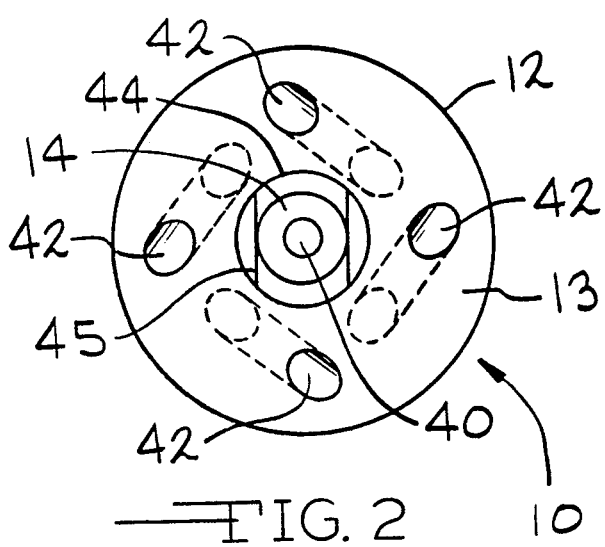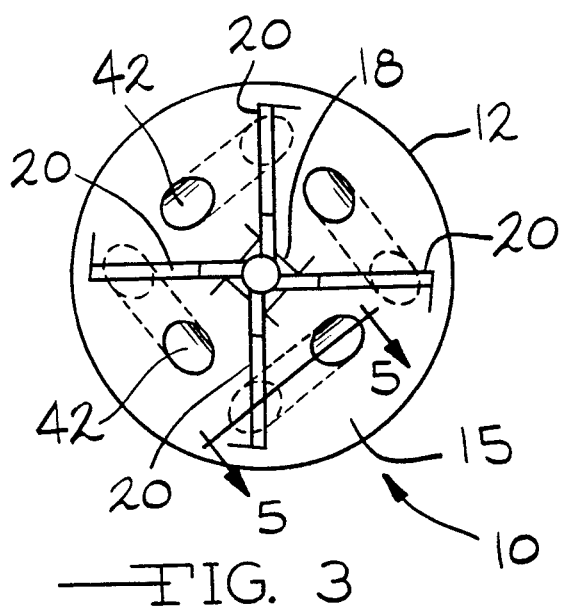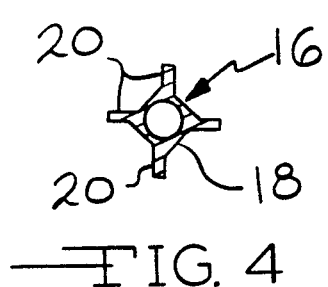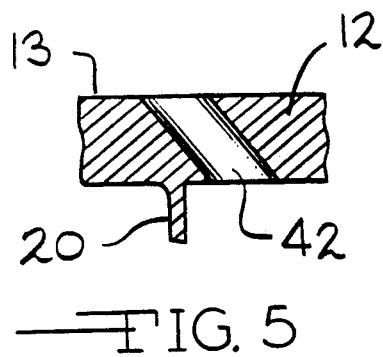

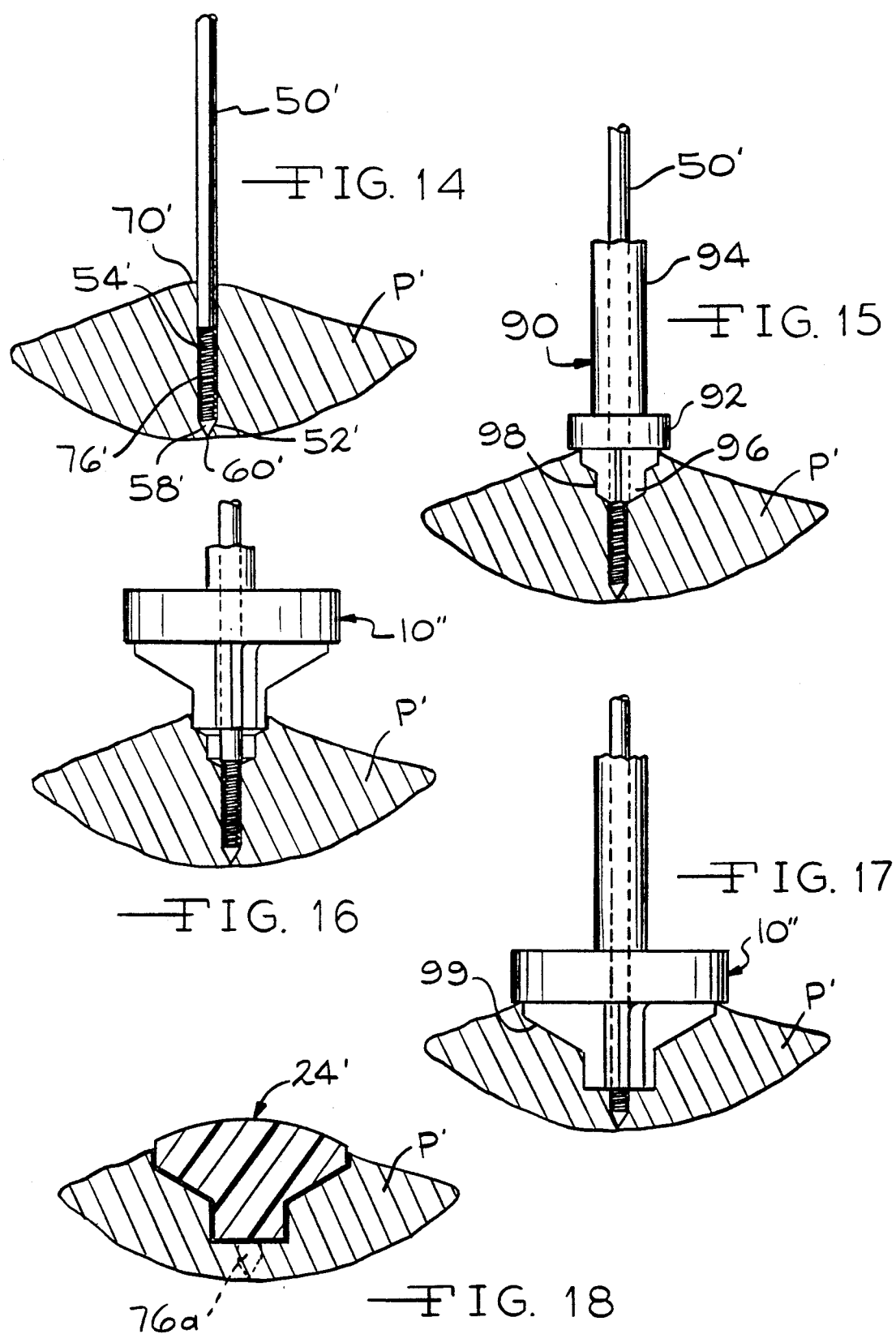

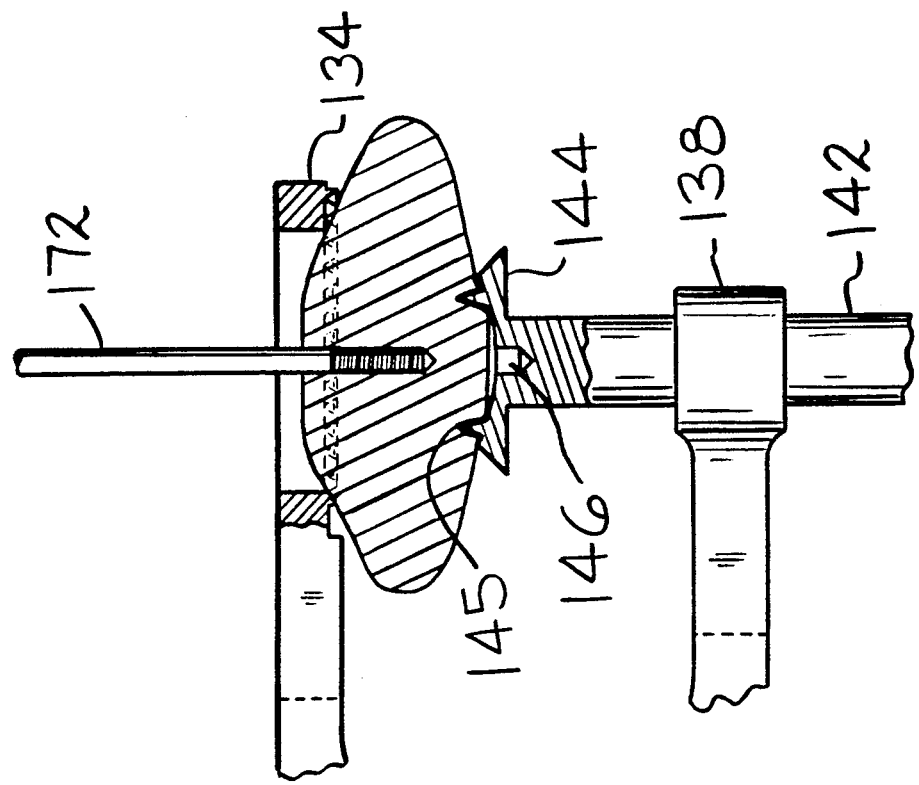
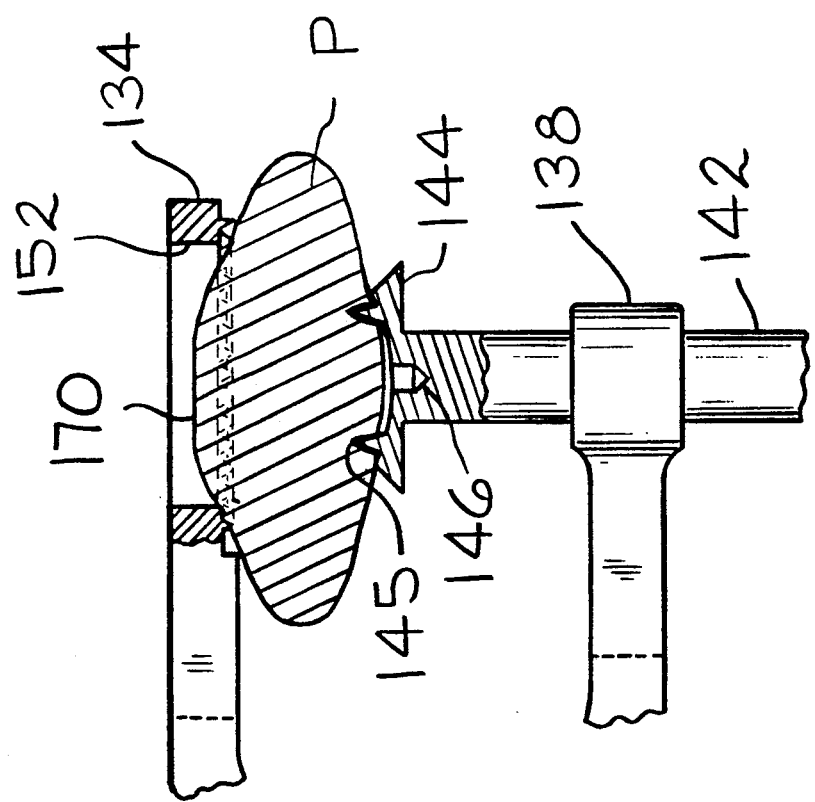

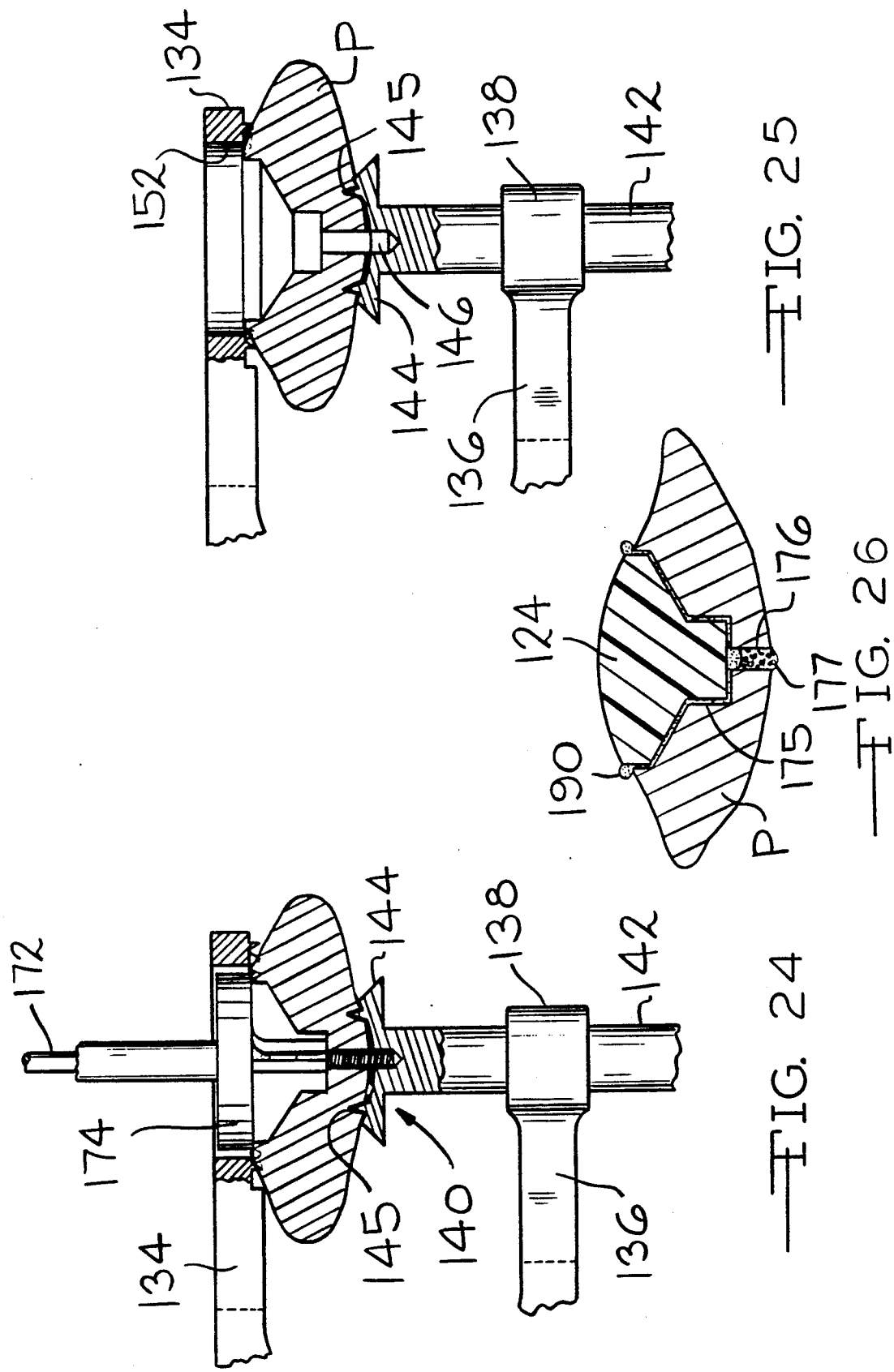

METHOD FOR IMPLANTING A PATELLAR PROSTHESIS

CROSS-REFERENCE TO RELATED APPLICATION

This application is a continuation-in-part of my co-pending U.S. application, Ser. No. 07/652,882, filed Feb. 8, 1991, now U.S. Pat. No. 5,180,384.

BACKGROUND ART

The present invention is directed to a method for implanting a patellar prosthesis in a human patella.

In total knee replacement surgery, a prosthesis is provided in which one component is fastened to the distal end of the femur which has been resectioned and another component is fastened to the proximal end of the tibia which has been resectioned so that the two components will act together in permitting the leg to bend and straighten out. In performing such surgery, the patella is not normally replaced but rather is resected such the interior crown portion facing the condyles is cut and reamed to form a cavity in which a patellar prothesis is implanted. The patellar prosthesis has a crown facing inwardly to engage the patellar or trochlear groove of the femoral component.

Heretofore, in preparing a patella for an implant, it was necessary to engage the patella with a clamp having a circular cross-sectional configuration and, using the interior surface of the clamp as a guide, ream a cavity in the patella of sufficient size to receive the patellar implant intended to be used. Depending upon a number of factors including the size of the patient, the patellar implant could be one of a number of different sizes. As a result of this, it was necessary to have available a number of clamps each having a different diameter for guiding various size reamers. Typical prior art methods of forming a cavity for implanting a patellar prosthesis are shown and described in the following publications, which are incorporated herein by reference: Brochures entitled "The AMK Total Knee System Design Rationale and Surgical Procedure" (page 25), DePuy, Division of Boehringer Mannheim Corporation, Warsaw, Ind, and "WHITESIDE ORTHOLOC a Modular KNEE SYSTEM", copyright 1989 by Dow Corning right, Arlington, Tenn. Copies of such references are herewith enclosed.

There has recently been introduced a new design of patellar prosthesis having a tapered surface on the side away from the crown. One such prosthesis is the subject matter of U.S. patent application Ser. No. 07/508,088, filed Oct. 18, 1990, by the applicant herein. The present method for implanting a patellar prosthesis is well-suited for implanting patellar prostheses of the type disclosed in such patent application; however, it should be understood that the method of the present invention is not so limited and may be used for implanting a wide variety of patellar prostheses. It has a significant advantage over the prior art for implanting a patellar prosthesis of a type in which one of a number of different sizes is to be used depending upon the patient in that the method of the present invention does not rely upon the patella clamp to guide the reamer. Accordingly, in utilizing the method of the present invention, it is not necessary to have available a plurality of clamps of varying sizes.

DISCLOSURE OF INVENTION

The present invention provides a new method for preparing a human patella for implanting a patellar prosthesis therein and a new method for implanting a patellar prosthesis in a human patella. As is well-known in performing knee replacement surgery, the patella is everted and retained in a position permitting the surgeon to have access to the articular surface which is normally engaged in the intercondylar notch between the condyles. Under the present invention, with the patella so supported, the surgeon, using a saw or similar tool for performing osteotomy, removes the top portion of the articular surface, thus leaving a flat surface near the central portion of the patella. Desirably, only a small portion of articular surface is removed in order to leave as much of the original patella intact as possible. Thus, as pointed out in the above-identified patent application, it is desirable that as little of the human patella be removed as possible.

Following removal of the top of the articular surface a threaded guidewire or pin is used to drill a passageway in the central portion of the patella at substantially right angles to the flat surface. Then, using the threaded guidewire which may be left in the passageway or a rod of similar size to that of the threaded guidewire positioned in said passageway, a cannulated reamer is placed over the threaded guidewire or other guide rod and, using such threaded guidewire or guide rod as a guide, the reamer is utilized to ream the patella thereby forming a cavity having a size and configuration suitable for receiving the patellar prosthesis. Following such reaming, the cavity is cleaned, bone cement placed therein and the patellar prosthesis implanted therein. If desired, the reaming could be performed in stages, initially using a reamer sized to form a relatively small cavity and thereafter using a reamer, sized to form the cavity for receiving the patella prosthesis.

It is also within the contemplation of the present invention to drill the passageway without cutting the apex of the articular surface or otherwise forming a flat surface.

Accordingly, it is an object of the present invention to provide a method for implanting a patellar prosthesis in a human patella.

It is it further object of the present invention to provide a method of cutting and reaming a patella in preparation for implanting a patellar prosthesis to provide accurate positioning while minimizing the amount of bone required to be removed.

It is a further object of the present invention to provide a method for preparing a patella for implantation of a patellar prosthesis without the necessity of using a patellar clamp for guiding the reamer.

Other objects and advantages of the present invention will become apparent from the following detailed description in conjunction with the attached drawings.

BRIEF DESCRIPTION OF THE DRAWINGS

FIG. 1 is an elevational view showing a cannulated reamer having cutting knives of a configuration suitable for implanting one type of patellar prosthesis.

FIG. 2 is a top plan view of the cannulated reamer of FIG. 1.

FIG. 3 is a bottom plan view of the cannulated reamer of FIG. 1.

FIG. 4 is a sectional view taken along line 4—4 of FIG. 1.

FIG. 5 is a fragmentary sectional view of the reamer head taken along line 5—5 of FIG. 3.

FIG. 14 is a sectional view of a patella during the initial step of a modified method of preparing a patella wherein a passageway is formed without first forming a flat surface.

FIG. 15 is a view similar to FIG. 14 showing one of a plurality of reaming steps using the threaded guidewire or other guide rod to guide the reamer during reaming.

FIG. 16 is a view similar to FIG. 15 showing the second reamer beginning to ream the final cavity.

FIG. 17 is a view similar to FIG. 16 showing completion of reaming the final cavity.

FIG. 18 is a sectional view showing a patellar prosthesis implanted in a patella prepared in accordance with the present invention.

FIG. 20 is a sectional view of a patella engaged by a patellar clamp.

FIG. 21 is a sectional view of the engaged patella during the initial step of drilling the guidewire into the patella.

FIG. 24 is a sectional view of the engaged patella showing the position of the cannulated reamer upon completion of the reaming step.

FIG. 25 is a sectional view of the engaged patella upon completion of the reaming step and removal of the cannulated reamer and guidewire.

FIG. 26 is a sectional view of a patella following placement of bone cement and a patellar prosthesis in the reamed cavity.

BEST MODE OF CARRYING OUT INVENTION

Figure 6:
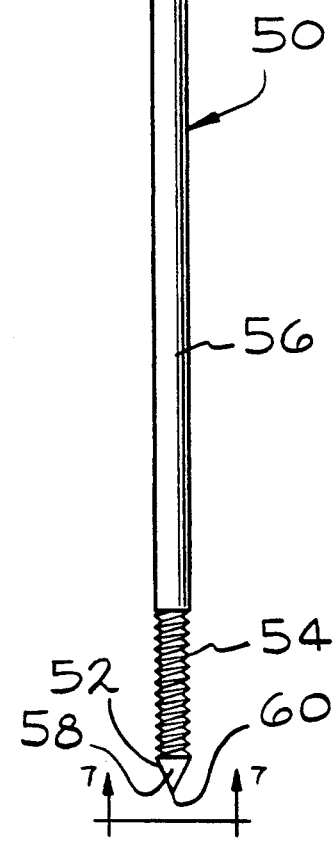
FIG. 6 is an elevational view showing the threaded guidewire for forming a guide passageway in the patella.

Referring now to FIGS. 1-5, there is shown a reamer generally designated by numeral 10 having a head 12 mounted on the end of a cannulated stem 14 extending along an axis A. The head 12 has an upper surface 13 and a lower surface 15. A cutting assembly 16 extends downwardly from the head 12 and includes a housing 18 and a plurality of cutting blades 20 integrally formed with and extending radially outwardly from the housing 18. In the embodiment of FIGS. 1-5, four cutting blades 20 are provided at substantially 90° from each other. As can be seen particularly in FIG. 1, the shape of the cutting blades are substantially identical and have a configuration tailored to form a cavity of a size and shape suitable for receiving the specific patellar prosthesis intended for implantation.

Figure 13:
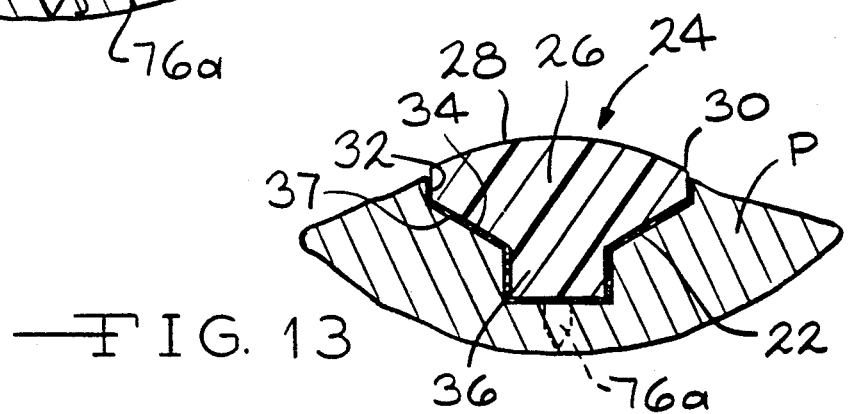
FIG. 13 is a sectional view showing a patellar prosthesis implanted in a patella prepared in accordance with the present invention.

For example, referring briefly to FIG. 13, there is shown a patella P in which a cavity 22 has been reamed and in which a patellar prosthesis 24 has been implanted utilizing the method of the present invention. The patellar prosthesis 24 of FIG. 13 has a body portion 26 with a dome 28 facing away from the patella P in a position to engage the patellar or trochlear groove of the femoral component of a total knee implant (not shown). The dome 28 terminates its outer periphery at an edge 30 which defines a circle from which a short cylindrical wall section 32 depends. As can be seen in FIG. 13 the edge 30 is preferably above the upper surface of the patella P about 1-2 mm; however, it could meet the upper surface of the patella and thus provide a smooth transition between the dome 23 and the upper surface of the patella P.

Tapering inwardly toward the central axis and downwardly in a direction away from the dome 28 is an inner wall surface 34 from which a stem 36 depends. The stem 36 may have one of a wide variety of shapes including the shapes shown in the brochures identified on page 1 hereof or the shape shown in my co-pending application Ser. No. 07/508,088 filed Oct. 18, 1990. A layer of bone cement 37 such as polymethylmethacrylate is used to bond the patellar prosthesis 24 in the cavity.

As will be appreciated from viewing FIG. 1 and FIG. 13, the cross-sectional shape of that portion of the patellar prosthesis 24 facing away from the dome 28 determines the shape defined by the cutting blades 20 and the shape of the cavity to be formed thereby. Thus, each of the blades 20 has a first cutting edge 20a substantially parallel to the axis A of the stem 14, a second cutting edge 20b tapering inwardly toward such axis A and away from the head 12, a third cutting edge 20c substantially parallel to such axis and a fourth cutting edge 20d extending radially inwardly from the third understood, edge 20c and joined to the housing 18. It should be understood, however, that the shape of the cutting blades 20 may vary depending upon the configuration of the patellar prosthesis intended to be implanted. In forming a cavity of the configuration shown in FIGS. 12 and 13 for receiving the prosthesis 24, the third cutting edge 20c and fourth cutting edge 20d will form a lower cylindrical portion of the cavity 22 intended to receive the stem 36, the second cutting edge 20b will form the portion of the cavity 22 flaring upwardly and outwardly from the lower cylindrical portion for receiving the portion of the prosthesis defined by the tapering inner wall surface 34 and the first cutting edge 20a will form the upper cylindrical portion of the cavity 22 for receiving the short cylindrical wall section 32 of the patellar prosthesis 24.

Figure 12:
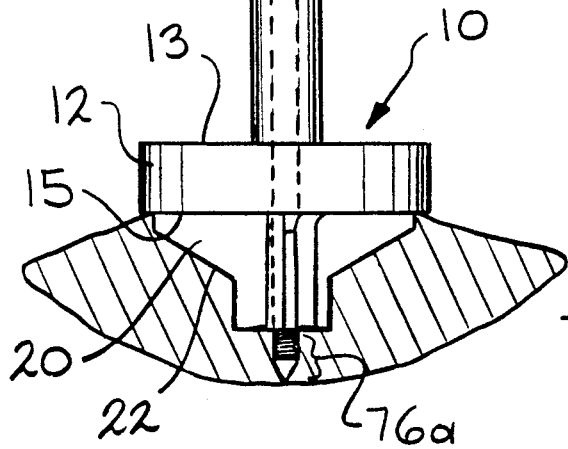
FIG. 12 is a view similar to FIG. 11 showing the reaming step using the drill bit or other guide rod to guide the reamer during reaming.

As can be seen in FIGS. 1 and 12, the cutting blades 20 do not extend outwardly to the outer periphery of the head 12. Thus, the first cutting edge 20a is closer to the axis A than is the outer periphery of the head 12. This construction permits the lower surface 15 to contact the patella P and function as a stop for determining the proper depth for the cavity 22 and insure against inadvertent reaming to an excessive depth.

The reamer 10 has a cylindrical passageway 40 extending throughout the stem 14, head 12 and housing 18. Additionally, the head 12 has a plurality of inclined passageways 42 extending therethrough from a position on the lower surface 15 between the cutting blades 20 and extending out of the upper surface 13. These inclined passageways 42 are intended to provide a means for expelling the debris from the cavity 22 being reamed. Thus, as the blades 20 ream the patella P, the bone material cut therefrom will be propelled into the end of the inclined passageway 42 at the lower face 15, through the inclined passageway 42 and out of it at the upper face 13.

The stem 14 of the reamer 10 has an enlarged area 44 which may be provided with opposing flat surfaces 45 for engagement by rotatable power means for rotating the head 12 and the cutting blades 20 carried thereby.

Figure 7:
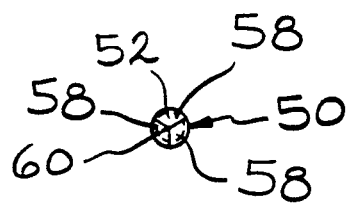
FIG. 7 is an end view of the threaded guidewire of FIG. 6 looking in the direction of the arrows 7—7.

Referring now to FIGS. 6 and 7, there is shown a threaded guidewire 50 having a cutting head 52, a helical thread 54 and an elongated shank 56 having a diameter slightly smaller than that of the cylindrical passageway 40 and a length sufficiently long to extend completely through the stem 14 of reamer 10. The cutting head 52 has three triangular shaped flats 58 extending to a tip 60 with the edges between the adjoining flats 58 functioning r as the primary cutters.

Figure 8:
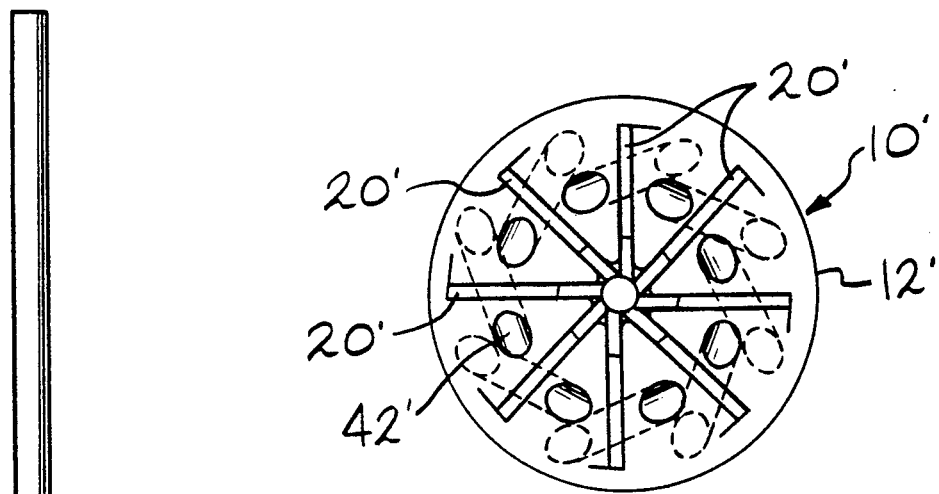
FIG. 8 is a view similar to FIG. 3 showing a modified reamer.
Figure 9:
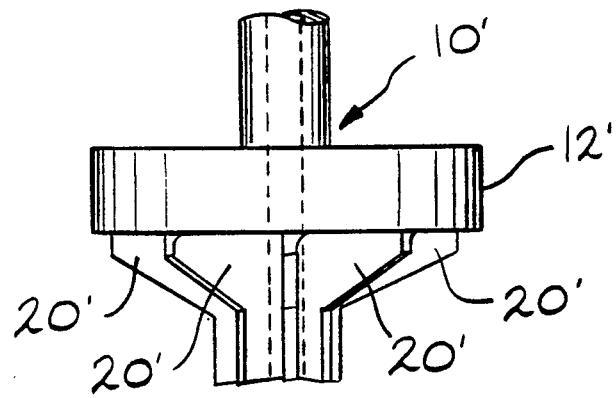
FIG. 9 is a fragmentary elevational view of the modified reamer of FIG. 8.

FIGS. 8 and 9 show a modified reamer 10' having a head 12' with eight cutting blades 20' as contrasted with the previous embodiment having four cutting blades 20. In this embodiment, there are provided eight inclined passageways 42' extending through the head for expelling debris during the cutting operation.

Figure 10:
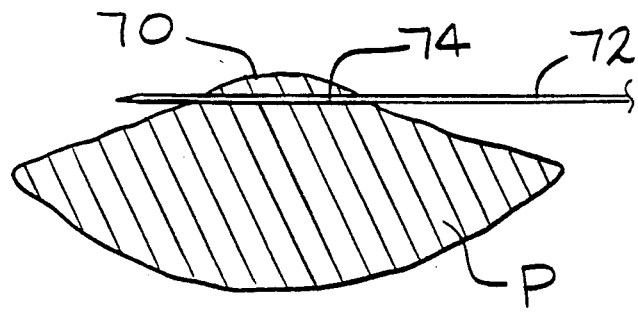
FIG. 10 is a sectional view of a patella during the initial step of removing the apex of the articular surface to form a flat surface.
Figure 11:
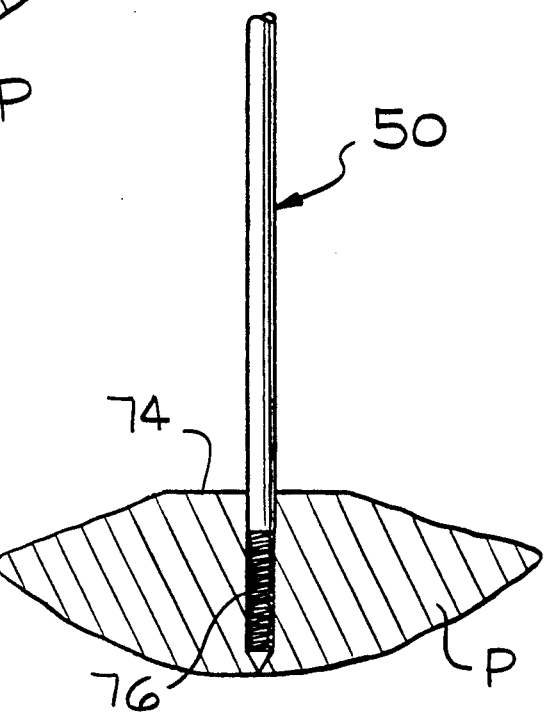
FIG. 11 is a view similar to FIG. 10 showing the next step of drilling a passageway at substantially right angles to the flat surface formed as shown in FIG. 10.

Referring now to FIGS. 10-12, there is shown a human patella P having an articular surface including an apex 70 which, in a normal knee prior to surgery, engages the intercondylar notch between the condyles at the distal end of the femur. According to the method of the present invention, the top of the apex 70 is cut with a standard cutting blade 72 to form a substantially plunar surface 74 as shown in FIGS. 10 and 11. Thereafter, the threaded guidewire 50 powered by a drill (not shown) is utilized to drill a passageway 76 in the patella P.

Following drilling of the passageway 76 the drill is disconnected from the threaded guidewire 50, leaving the threaded guidewire 50 in the passageway 76. Then, using the threaded guidewire 50 as a guide, the reamer 10 is placed thereover and is connected to power means which rotates it thereby causing the cutting blades 20 to form the cavity 22 having a configuration determined by the configuration of the cutting edges 20a, 20b, 20c and 20d of cutting blades 20. In the drawings it is shown as having the desired configuration to receive the patellar prosthesis 24. During such cutting the threaded guidewire 50, snugly received in the passageway 40, serves to accurately guide the reamer 10 on the correct axial path in reaming the patella P to form the cavity 22. Thus, the threaded guidewire 50 prevents the reamer 10 from drifting off such path and forming a larger cavity than desired. As previously noted, during such reaming process, debris will be expelled through the included passageways 42 extending through the head 12. Completion of the reaming step occurs when the lower surface 15 of the head 10 engages the patella P. As previously noted, the design of the reamer head 12 to cause engagement of such lower surface 15 with the articular surface of the patella P, prevents the reamer from reaming to a greater depth than desired.

Following completion of the reaming step, the reamer 10 and the threaded guidewire 50 are removed, the cavity 22 is cleaned of debris and prepared in accordance with standard surgical implantation techniques including application of bone cement such as polymethylmethacrylate and affixing of the patellar prosthesis 24 therein. Preferably, prior to placing bone cement in the cavity 22, pulverized bone chips and/or bone slurry will be placed in the end portion 76a of the passageway 76 extending below the bottom of that portion of the cavity 22 formed by the lower cutting edge 20d. Such bone chips and/or bone slurry serve as a graft inducing bone growth into such end portion 76a. However, it is possible that such end portion be filled only with bone cement.

Irrespective of whether the cutting head has four cutting blades 20 shown in the embodiment of FIGS. 1-5, or eight cutting blades 20' shown in the embodiment of FIGS. 8 and 9 or fewer or more of such cutting blades, the method set forth pursuant to the present invention permits the implantation of a patellar prosthesis in a highly accurate manner with a minimal removal of bone.

Referring now to FIGS. 14-18, there is shown a modified method for preparing a patella P' and for implanting a patellar prosthesis 24' therein.

As shown in FIG. 14, there is provided a threaded guidewire 50' having a head 52' with cutting flats 58' extending to a tip 60'. A helical thread 54' extends upwardly from the head 52'.

Under this embodiment, the apex 70' of the patella P' is not cut to form a flat surface as in the previous embodiment, but rather the threaded guidewire 50' directly engages the articular surface at a desired location in the vicinity of the apex 70. As will be appreciated by those skilled in the art, during this step, the patella P' will be held by a suitable clamping mechanism while the drill powering the threaded guidewire 50' is used to form a passageway 76' in the patella P'.

The drill is then disconnected from the threaded guidewire 50' and a first or pilot reamer 90 having a head 92 mounted on the end of a cannulated stem 94 is positioned over the threaded guidewire 50'. The head 92 has a plurality of cutting blades 96 extending downwardly therefrom. As can be seen from FIG. 15, the head 92 and cutting blades 96 of the pilot reamer 90 are much smaller than required to form a cavity of the size intended for the patellar implant 24' as shown in FIG. 18. Thus, the first or pilot reamer 90 forms a relatively small cavity 98. As shown in FIGS. 16 and 17, a second reamer 10'' similar or identical to the reamer 10 of the embodiment of FIGS. 1-13 is provided to form a final cavity 99 having a size and configuration suitable for receiving the patellar implant 24'. It may be preferable to the surgeon to perform the reaming in two steps, particularly if the surgeon does not wish to form the flat surface by cutting the apex of the articular surface. In performing the reaming in two steps, the surgeon forms first a relatively small cavity 98 using the threaded guidewire 50' or other guide means positioned in the passageway 76' to guide the direction of the first or pilot reamer 90 and thereafter forming the final cavity 99 with reamer 10' again using the threaded guidewire 50' or other guide means. As in the previous embodiments the end portion 76a is preferably filled with bone chips or bone slurry to serve as a graft inducing bone growth therein.

Although the method has been described using a cannulated reamer 10 with flat cutting blades 20, it should be understood that a wide variety of reamers could be used. For example, a convex grater type reamer with a cannulated center to accommodate the guidewire is one which could be used.

Figure 19:
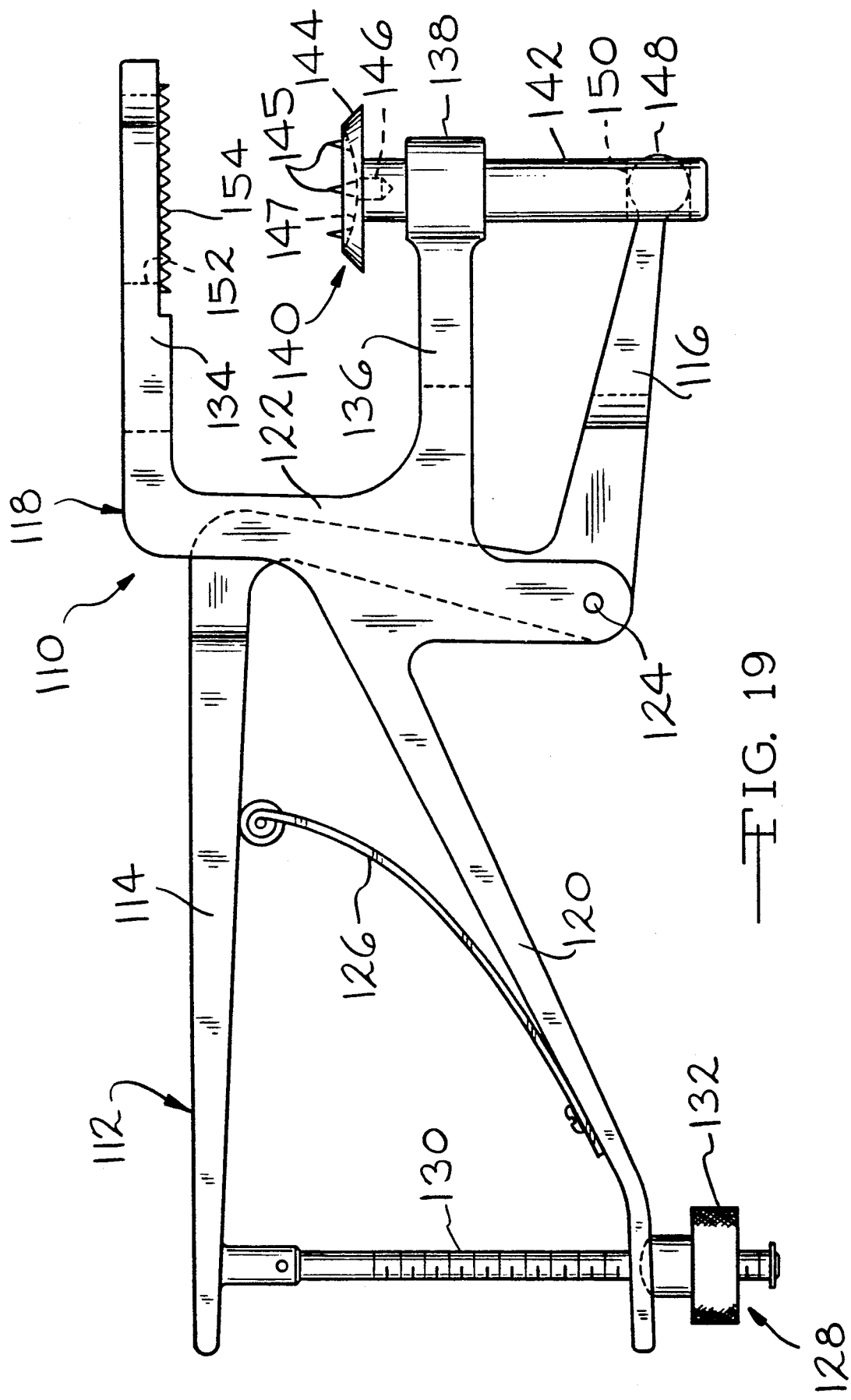
FIG. 19 is an elevational view of a patellar clamp for engaging a patella.

Referring now to FIG. 19, there is shown a patellar clamp generally designated by numeral 110. The clamp 110 is constructed of two distinct units: a generally Z-shaped member 112 forming an upper grip member 114 at one extreme and pivot arm 116 at the opposed extreme; and a second member 118 generally shown to form a lower grip member 120 at one extreme and a generally U-shaped clamping member 122 at the opposed extreme. The Z-shaped member 112 and the second member 118 are pivotally interconnected at pivot point 124. A resilient means 126 is positioned between the upper grip member 114 and lower grip member 120, acting to force the upper and lower grip members 114, 120 in an outwardly expansive resting position. It can be seen from viewing FIG. 19 that the farther the upper grip member 114 and the lower grip member 120 are separated, the farther the pivot arm 116 will be positioned away from the clamping member 112. A locking member 128 consisting of a bolt 130 and thumb nut 132 is engaged with the upper grip member 114 and lower grip member 120 to provide the specific desired limitations on the outward expansion of the grip members 114, 120 as caused by the resilient member 126.

The clamping member 122 is, preferably, shown to be of a generally U-shaped configuration defining an articular surface clamping member 134 integrally formed along one of the arms of the U. The opposed arm 136 of the U-shape extends parallel to the articular surface clamping member 134. The opposed arm 136 defines a centering member 138 which is positioned on the centerline axis of the articular surface clamping member 134. An anterior or subcutaneous clamping member 140 is engaged by the centering member 138. The anterior clamping member 140 includes a shaft 142 having a cup-shape unit 144 formed at the end closest in proximity to the articular surface clamping member 134. The end of the shaft 142 opposed to the cup-shape unit 144 is engaged with the pivot arm 116. The cup-shape unit 144 further includes a plurality of spike members 145 extending upwardly from the surface 147 of the cup-shape unit 144. The spike members 145 are preferably 2 to 4 mm in length.

A hole or indent 146 is formed in the cup-shape unit 144 at the centerline axis of the articular surface clamping member 134. Preferably, the hole is 4 to 6 mm in diameter and 4 to 6 mm deep.

The engagement between the shaft 142 and the pivot arm 116 is achieved by means of a sliding pivot joint. The pivot joint consists of a ball member 148 is engaged in a retention slot 150 which allows the ball member 148 to slide in the retention slot 150 in a direction transverse to the movement of the shaft 142 along the centerline axis of the articular surface clamping member 134.

The articular surface clamping member 134 is generally donut shaped, defining a center aperture 152 having an inner diameter measuring 31-36 mm. The engagement surface 154 of the articular surface clamping member 134 is preferably serrated completely around the surface. The depth of the serrations are 2 to 4 mm. Alternatively, the serrations may only be partially located around the engagement surface 154 of the clamping member 134.

Referring now to FIG. 20, a human patella P is shown as it is engaged by the patellar clamp. As shown in FIG. 20, the top of the apex of the patella has been removed to form a substantially planar surface 170. However, as previously mentioned, it is not necessary that such apex be removed. The patellar clamp articular surface clamping member 134 is positioned to engage the articular surface of the patella P. Upon achieving the proper positioning of the articular surface clamping member 134, the upper grip member 114 and lower grip member 120 are squeezed together to cause the pivot arm 116 to drive the anterior clamping member 140 into engagement with the subcutaneous tissue of the patella. The spike members 145 insert into the tissue to prevent slippage of the patella while clamped between the articular surface clamping member 134 and anterior clamping member 140. Once proper tension between the clamping members 134, 140 has been achieved, the thumb nut 132 of the locking member 128 is tightened to prevent the upper grip member 114 and lower grip member 120 from separating.

Figure 22:
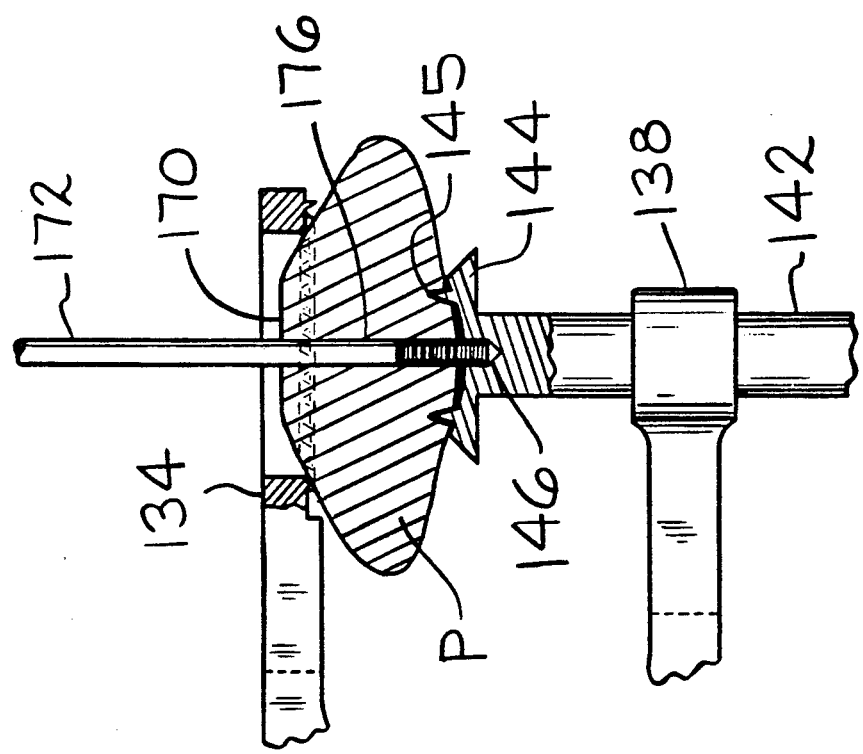
FIG. 22 is a sectional view of the engaged patella with the guidewire in its final position.

Referring now to FIG. 21, the drilling with a combination guidewire and drill 172 has begun. As shown in FIG. 22, the guidewire/drill 172 forms a passageway 176 extending completely through the patella P and into the hole 146 where it is retained in aligned position with the centerline axis of the articular clamping member 134. If desired, a universal patellar clamp of the type disclosed in my co-pending application Ser. No. 07/779,352, filed Oct. 18, 1991, incorporated herein by reference, may be used for supporting the patella in the everted position during the procedure. If such universal clamp is used, the guide arms defining a centering guide hole may be used for guiding the guidewire/drill 172 in forming the passageway 176.

Figure 23:
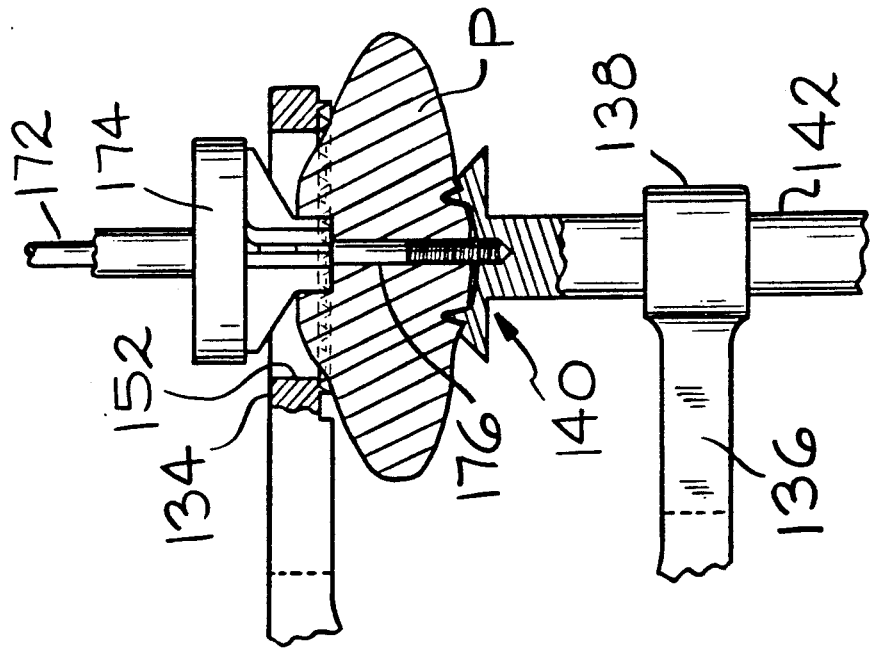
FIG. 23 is a sectional view of the engaged patella with a cannulated reamer positioned over the guidewire during reaming.

Referring now to FIG. 23, with the guidewire/drill 172 in its final position extending through the patella P and into the hole 146 of the cup-shape unit 144, a cannulated reamer 174 is positioned over the guidewire 172 and is placed in position within the center aperture 152 of the articular surface clamping member 134 for properly reaming the patella.

Referring now to FIGS. 24 and 25, the reaming step is completed and the cannulated reamer 174 and guidewire 172 are shown in their final positions in the patella P. After the cannulated reamer 174 and guidewire 172 are removed, the patella P is left with the appropriate cavity for receiving the patellar prosthesis.

Referring now to FIG. 26, there is shown the patella P with the patellar prosthesis 124 implanted therein with polymethylmethyacrylate bone cement 175 forming a bond between such patellar prosthesis 124 and the patella P. As is well-known in the art, the bone cement is positioned in the bottom of the newly formed cavity prior to placement of the patellar prosthesis 124 therein. Following placement of the patellar prosthesis 124 in the newly formed cavity, uniform and even compressive as well as axial pressures are applied to the dome of the patellar prosthesis 124 to force it completely into the cavity. The result of such forcing of the patellar prosthesis in such cavity is to cause the bone cement 175 to be pressurized between the wall of the cavity and the adjacent surfaces of the patellar prosthesis 124. The passageway 176 will act as a vent to allow excess marrow fat, blood and debris 177 remaining in the cavity to be forced out of the cavity and thus not interfere with the bonding between the cement and bone. This will allow osseointegration and optimal bonding between the cement and the bone and the ultimate sound fixation of the patellar prosthesis to the reamed cavity. Additional amounts of excess bone cement which have flowed to the outer periphery of the patellar prosthesis may be forced out of the portion of the cavity adjacent the articular surface as shown at 190 in FIG. 26.

Many modifications and embodiment will become readily apparent to those skilled in the art. Accordingly, the scope of the present invention should be determined only by the scope of the appended claims.

I claim:

1. A method of implanting a patellar prosthesis in a human patella having a first side with an articular surface and central apex and a second side generally opposite said first side comprising:
   (a) providing a patellar prosthesis having a body portion including an upper side with a dome and a lower side with a stem extending therefrom;
   (b) drilling a passageway extending through said patella from said first side in the vicinity of said central apex to said second side, said passageway forming an outlet at said second side for permitting drainage of debris;
   (c) providing elongated guide means in said passageway;
   (d) providing a reamer having a head, cutting means depending from said head and a central cannulation extending through said cutting means and said head, said cannulation having a size to fit over said elongated guide means;
   (e) positioning said reamer over said elongated guide means and reaming a cavity in said patella having a size and configuration to receive said patellar prosthesis while using said guide means as a guide;
   (f) placing bone cement in said cavity; and
   (g) placing said patellar prosthesis in said cavity and applying pressure to said dome to urge said patellar prosthesis further into said cavity and squeeze said bone cement into bonding relationship with said patella and permitting excess marrow fat, blood and debris to flow out of said passageway outlet.

2. The method according to claim 1, further including the step of engaging said elongated guide means in centering means positioned adjacent said passageway outlet and retaining it in said centering means during said reaming step.

3. The method according to claim 1, further including the step of engaging said articular surface with stop means when said cavity has been reamed to a size to receive said patellar prosthesis.

4. The method according to claim 1, wherein said r r reaming step includes:
   (a) reaming a first pilot cavity having a size smaller than said cavity.

5. The method according to claim 1, wherein said patellar prosthesis has a tapering surface opposite said upper dome which tapers upwardly toward said upper dome as it extends radially outwardly from said stem and permitting said bone cement to flow upwardly and outwardly along said tapering surface during the step of applying pressure to said dome.

6. A method of preparing a patella having an articular surface with an apex and an opposite side for a patellar prosthesis implant comprising:
   (a) engaging said patella with a clamp having an enlarged opening through which access to a central portion of said articular surface may be had;
   (b) forming an elongated passageway extending through said patella from said articular surface to an outlet at said opposite side for permitting drainage of debris;
   (c) positioning elongated guide means in said passageway;
   (d) positioning over said elongated guide means a cannulated reamer having a cannulation with the elongated guide means extending through said cannulation, said cannulated reamer extending through said clamp enlarged opening;
   (e) reaming a cavity in said patella having a size and configuration to receive said patellar prosthesis while using said guide means as a guide.

7. The method according to claim 6, further including the step of engaging said elongated guide means in centering means positioned adjacent said passageway outlet and retaining it in said centering means during said reaming step.

8. The method according to claim 6, further including the step of engaging said articular surface with stop means.

9. The method according to claim 6, wherein said reaming step includes:
   (a) reaming a first pilot cavity having a size smaller than said cavity.

10. A method of preparing a patella to receive a patellar prosthesis implant, said patella having a first side with an articular surface and an opposite side opposing said articular surface, comprising:
    (a) forming an elongated passageway in said patella from said first side to an outlet at said opposite side for permitting drainage of debris:
    (b) positioning elongated guide means in said passageway;
    (c) reaming a cavity in said patella having a size and configuration to receive said patellar prosthesis while using said guide means as a guide.

11. The method according to claim 10, wherein the step of reaming said cavity includes the step of providing a cannulated reamer having a cannulation and positioning said reamer such that said elongated guide means extends through said cannulation.

12. The method according to claim 10, further including the step of engaging said elongated guide means in centering means positioned in said passageway outlet.

13. The method according to claim 10, wherein the step of reaming said cavity includes providing means having stop means limiting the depth of said reaming and engaging said articular surface with said stop means.

14. The method according to claim 10, wherein said reaming is performed in two steps including:
    (a) reaming a first pilot cavity having a size smaller than said cavity; and thereafter,
    (b) reaming said cavity.

15. A method of implanting a patellar prosthesis in human patella having a first side with an articular surface and an opposite side opposing said articular surface, comprising:
    (a) providing a patellar prosthesis having a body portion including an upper side with a dome and a lower side with a stem extending therefrom;
    (b) drilling a passageway through said patella from a first opening on said first side to a second opening on said opposite side for permitting drainage of debris;

(c) positioning elongated guide means in said passageway;

(d) reaming a cavity in said patella having a size and configuration to receive said patellar prosthesis while using said guide means as a guide;

(e) placing bone cement in said cavity;

(f) placing said patellar prosthesis in said cavity and applying pressure thereto to urge said patellar prosthesis into bonded relationship with said patella and permitting marrow fat, blood and debris to flow out of said second opening.

16. The method according to claim 15, wherein the step of reaming said cavity includes the step of providing a cannulated reamer having a cannulation extending along the path of reaming and positioning said reamer such that said elongated guide means extends through said cannulation.

17. The method according to claim 15, further including the step of engaging said elongated guide means in centering means positioning adjacent said second opening and retaining it in said centering means during said reaming step.

18. The method according to claim 15, wherein the step of reaming said cavity includes providing reaming means having stop means limiting the depth of said reaming and engaging said articular surface with said stop means.

19. The method according to claim 15, wherein said patellar prosthesis has a tapering surface opposite said upper dome which tapers upwardly toward said upper dome as it extends radially outwardly from said stem and permitting said bone cement to flow upwardly and outwardly along said tapering surface during the step of applying pressure.

20. In a method of preparing a patella to receive a patellar prosthesis, said patella having a first side with an articular surface an opposite side opposing said articular surface, wherein a cavity is formed in said patella inwardly from said articular surface for receipt of said patellar prothesis, the improvement comprising forming a passageway communicating with said cavity and extending through said patella to an outlet at said opposite side for permitting drainage of debris.

21. In method of implanting a patellar prothesis in a human patella having a first side with an articular surface and an opposite side opposing said articular surface wherein a cavity is formed in said patella inwardly from said articular surface, and a patella prothesis having a body portion including an upper side with a dome and a lower side with a stem extending therefrom is secured in said cavity, the improvement comprising forming a passageway communicating with said cavity and extending through said patella to an outlet at said opposite side and placing said patellar prosthesis in said cavity and applying pressure thereto to urge said patellar prothesis into bonded relationship with said patella and permitting marrow fat, blood and debris to flow out of said outlet.

* * * * *